US00H002218H

(19) United States
(12) Statutory Invention Registration
Hwang et al.

(10) Reg. No.: US H2218 H
(43) Published: Jun. 3, 2008

(54) GLUCOSAMINE AND METHOD OF MAKING GLUCOSAMINE FROM MICROBIAL BIOMASS

(76) Inventors: Ki-Oh Hwang, 727 71st St. NE., Cedar Rapids, IA (US) 52402; James Donald Steinke, 6010 Teakwood Ct. NE., Cedar Rapids, IA (US) 52402; Joseph P. Henning, 19167 Columbia Rd., Eddyville, IA (US) 52553; John A. Bohlmann, 472 E. Rochester, Ottumwa, IA (US) 52501; James R. Trinkle, 2290 Van Buren Dr., Bussey, IA (US) 50044; Weiyu Fan, 4117 Highland Rd., Minnetonka, MN (US) 55345

(21) Appl. No.: 10/382,251

(22) Filed: Mar. 5, 2003

(65) Prior Publication Data

US 2003/0181419 A1 Sep. 25, 2003

Related U.S. Application Data

(60) Provisional application No. 60/362,206, filed on Mar. 5, 2002.

(51) Int. Cl.
*A61K 31/7008* (2006.01)
*C07H 5/04* (2006.01)

(52) U.S. Cl. ..... 514/62; 536/55.2

(58) Field of Classification Search ..... 536/55.2, 536/55.3; 514/62

See application file for complete search history.

(56) References Cited

U.S. PATENT DOCUMENTS 4,806,474 A * 2/1989 Hershberger ..... 435/101

5,905,035 A * 5/1999 Okada et al. ..... 435/254.1

FOREIGN PATENT DOCUMENTS

WO WO 98/30713 * 7/1998

OTHER PUBLICATIONS

Nikolaeva et al. "Preparation of glucosamine from shrimp sheels, and its use in medicine," Trudy Vniro, 1967, pp. 165–169, Abstract, Caplus, AN 1968:62641.*

Biochemicals and Reagents for Life Science Research, Sigma, p. 499.*

* cited by examiner

*Primary Examiner*—Michael J. Carone
(74) *Attorney, Agent, or Firm*—Paula A. DeGrandis

(57) ABSTRACT

Glucosamine suitable for human or animal consumption is disclosed. The glucosamine is derived from microbial biomass containing chitin. Suitable starting materials include substantially uniform microbial fungal sources, such as fungal sources derived from *Aspergillus* sp., *Penicillium* sp., *Mucor* sp. and combinations thereof. Methods of producing glucosamine by acid hydrolysis of fermented fungal biomass are also disclosed.

27 Claims, 6 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

Glucosamine and Glucose from Biomass after Hydrolysis at reflux condition

GLUCOSAMINE AND METHOD OF MAKING GLUCOSAMINE FROM MICROBIAL BIOMASS

CROSS REFERENCE TO RELATED APPLICATIONS

This application claims priority to Provisional Application Ser. No. 60/362,206 filed Mar. 5, 2002.

FIELD OF THE INVENTION

The present invention is directed to glucosamine compositions and to methods of making glucosamine compositions.

BACKGROUND

Glucosamine is a nutraceutical supplement that has been shown to provide significant therapeutic relief for arthritis and joint pain. Although the mechanism is not entirely known, it is believed that glucosamine functions to aid in restoration of the cartilage to relieve inflammation in the joints, thereby providing significant benefit to patients.

Presently, glucosamine is primarily derived from harvested natural sources, such as shellfish and other aquatic organisms. Components of the shell or exoskeleton of these organisms are converted into glucosamine using various production techniques. These natural sources are acceptable for producing glucosamine for some applications, but they have limitations. These limitations include the fact that wild shellfish can have significant variations in their composition because they grow naturally under uncontrolled circumstances. The shellfish can vary in such aspects as their size and composition depending upon the growing conditions as well as their species. Also, without control over the growing conditions, the shellfish can be exposed to environmental contaminants, including heavy metals, that can be retained in glucosamine or other products produced from the shellfish. Shellfish harvests are often seasonal, and thus the supply and price of shellfish shows significant variation over time.

A further concern with glucosamine derived from shellfish is that significant portions of the human population have shellfish allergies and are unable to use products that contain ingredients derived from shellfish. Highly processed materials, such as glucosamine, do not necessarily provide any allergic risk when prepared properly; but a concern remains that hyper allergenic individuals will still be allergic to even minute traces of allergens present from the original shellfish. Even if no such allergens are present, glucosamine derived from shellfish can pose a concern to individuals who are allergic to shellfish because individual consumers are not necessarily aware of whether or not all of the allergens have been removed.

An additional problem associated with existing sources of shellfish-derived glucosamine is that some of the shellfish supply is harvested from the seas and oceans of the world. Excessive harvest of shellfish could have a great negative environmental impact. Thus, it is believed that some consumers would prefer to use glucosamine that is not harvested at the expense of sea life. Even if the environmental impact of harvesting shellfish is not negative, there remains concern that the supply of wild shellfish is limited in quantity and inconsistent in quantity from year to year.

Therefore, a need exists for a source of safe, consistent, high quality glucosamine that can be created economically and with a minimum of environmental impact.

SUMMARY OF THE INVENTION

The present invention is directed to glucosamine, including glucosamine-containing material suitable for human or animal consumption. Glucosamine of the present invention is derived from fermented microbial biomass containing chitin and/or mureins. Suitable starting materials include substantially uniform microbial fungal sources, bacterial sources, and mixtures thereof. More specifically, fungal sources derived from *Aspergillus* sp., *Penicillium* sp., *Mucor* sp., and combinations thereof can be used. Use of either bacterial biomass or fungal biomass results in a high quality product that produces generally uniform glucosamine having low levels of impurities. The glucosamine of the present invention normally has relatively low ash content, and low heavy metal content. In addition, as a product of fungal biomass, the glucosamine does not pose a hazard to persons who have shellfish allergies.

The present invention is also directed to methods of producing glucosamine by acid hydrolysis of fermented microbial biomass. The methods of obtaining glucosamine from microbial biomass include reacting chitin or murein-containing biomass in an acidic solution, in particular reacting the chitin or murein-containing biomass in acid at an elevated temperature.

Other features and advantages of the invention will be apparent from the following detailed description of the invention and the claims. The above summary of principles of the disclosure is not intended to describe each illustrated embodiment or every implementation of the present disclosure. The detailed description that follows more particularly exemplifies certain embodiments utilizing the principles disclosed herein.

DRAWINGS

The invention will be more fully explained with reference to the following drawings, in which:

FIG. 1 is chart showing the percent yield of glucosamine over time of an example method of making glucosamine in accordance with the invention. The Y axis provides the % yield of glucosamine as calculated from the pre-cooking dry weight. The pre-cooked dry weight was taken [WHEN IN THE PROCESS WAS THE WEIGHT TAKEN see Joe's comments on hard copy]

Figure 1:
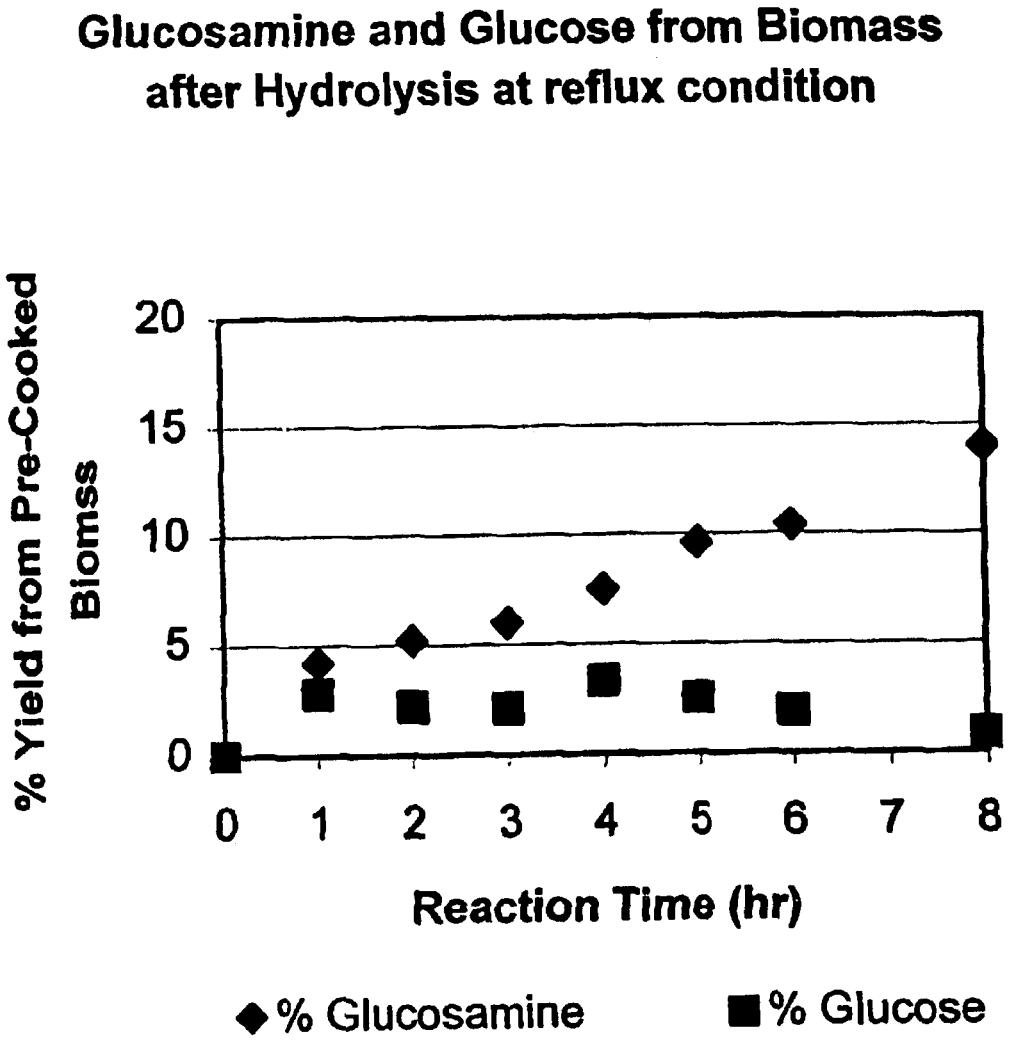

While principles of the invention are amenable to various modifications and alternative forms, specifics thereof have been shown by way of example and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The present invention is directed to glucosamine, including glucosamine-containing material suitable for human or animal consumption. The glucosamine can be derived from chitin present in various types of fungal biomass and/or murein derived from various types of bacterial biomass. Chitin is a natural polysaccharide, with the structure of an unbranched polymer of 2-acetoamido-2-deoxy-D-glucose (N-acetyl-D-glucosamine). This formula can be represented by the general repeating structure:

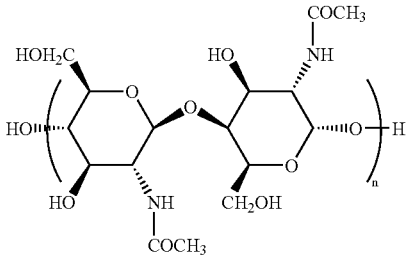

Chitin is typically an amorphous solid that is largely insoluble in water, dilute acids, and alkali. Although chitin has various commercial applications, greater commercial utility can be found by transforming the polymeric structure into individual components of 2-amino-2-deoxy-D-glucose, which is known as glucosamine.

Structurally, glucosamine is modified glucose with an amine group replacing the OH group found on carbon two (C-2). The general structure is:

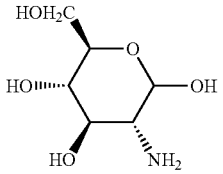

As stated above, glucosamine of the present invention can be derived from fermented fungal biomass containing chitin. Suitable starting materials include substantially uniform microbial fungal sources, such as fungal sources derived from *Aspergillus* sp., *Penicillium* sp., *Mucor* sp. and combinations thereof. Use of a fungal biomass results in a high quality product that produces a generally uniform glucosamine having low levels of impurities. The glucosamine of the present invention normally has relatively low ash content, and low heavy metals content. In addition, as a product of fungal biomass, the glucosamine does not pose a hazard to persons who have shellfish allergies.

The glucosamine composition, starting materials, and production methods will now be described in greater detail A. Glucosamine The glucosamine of the present invention is derived from relatively uniform microbial biomass sources, and thus typically has a generally uniform composition. Depending upon the methodology used to purify the glucosamine or desired glucosamine salt; the resulting glucosamine containing composition can be produced with varying levels of purity, including compositions that exceed 95 percent purity, 98 percent purity, and even 99.8 percent purity. The glucosamine compositions can also contain additional ingredients, such as additional salts. In such circumstances the overall purity of the desired composition relative to undesirable impurities can be maintained at levels that exceed 95 percent purity, 98 percent purity, and even 99.8 percent purity.

The glucosamine of the present invention has the general formula represented below:

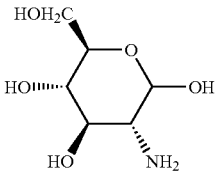

This general formula can vary depending upon the presence of various salts of the glucosamine, including citrate, acetate, phosphate, sulfate, chloride, lactate, gluconate, etc. Also, the glucosamine can be substituted or modified without diverging from the scope of the invention. Thus, as used herein, the term glucosamine refers to the various forms of glucosamine, including salt complexes and substituted glucosamine.

The glucosamine is normally of high purity, but can contain other ingredients, including glucose, unreacted chitin, and other materials. Preferably the glucosamine contains less than 10 percent glucose, more preferably less than 5 percent glucose, and even more preferably less than 2 percent glucose.

The glucosamine of the present invention has a relatively low ash content. The ash content is usually less than 5 percent, more typically less than 2 percent, and can even be less than 1 percent in some implementations. Heavy metal content is normally similarly low, typically well below 100 parts per million, more typically below 50 parts per million, even more typically below 20 parts per million. In certain embodiments this level is below 10 parts per million. The glucosamine can have a positive specific rotation, such as a positive 69 to 74 degree specific rotation for the glucosamine hydrochloride salt. The glucosamine of the invention is usually relatively white in its purified dry form, but colorless when dissolved in an aqueous solution. In one example, a 20 percent by weight solution of the glucosamine has an American Public Health Association (APHA) color of less than 50.

B. Microbial Biomass Starting Materials

1. Fungal

Suitable starting materials include substantially uniform microbial biomass sources, typically fungal biomass, such as filamentous fungi having greater than 10 percent chitin by total dry cell weight, such as fungal sources derived from *Aspergillus* sp., *Penicillium* sp., *Mucor* sp. Suitable fungal biomasses include *Aspergillus niger, Aspergillus terreus, Aspergillus oryzae, Mucor rouxii, Penicillium chrysogenum, Penicillium notatum, Saccharomyces cerevisiae; Saccharomyces uvarum;* and in particular *Candida guillermondi, Aspergillus niger,* and *Aspergillus terreus.* The biomass is usually recovered from a commercial fermentation reaction, such as the commercial production of organic acids, including citric acid. Also, the biomass suitable for production of glucosamine can be generated specifically for this process and not as a byproduct of other processes. As used herein, the term microbial does not include phyto-plankton and crustaceans or mollusks.

The invention is particularly well suited to uses where the chitin levels in the biomass exceed 5 percent of the dry biomass weight. Such biomass usually has between 5 and 25 percent chitin, and can have from 10 to 20 percent chitin, based upon dry weight of the biomass. Also, in order to prepare the highest quality glucosamine, it is sometimes desirable that the microbial biomass be produced in a substantially controlled manner having relatively uniform temperature and nutrient levels during the growth of the biomass.

2. Bacterial

Suitable starting materials include bacterial biomass that is derived from bacteria that have cells walls containing murein. Mureins are biological heteropolymers that contain N-acetylglucosamine as one of their components. Bacteria that are Gram positive, as well as actinomycetes (actinomycetes are Gram +) are useful as starting materials.

The invention is particularly well suited to uses where the murein levels in the cell wall of the bacteria exceeds 5 percent of the total dry weight of the wall. The total dry weight of the wall usually has between 25 and 50 percent murein, and can have greater than 50 percent murein. Also, in order to prepare the highest quality glucosamine, it is sometimes desirable that the microbial biomass be produced in a substantially controlled manner having relatively uniform temperature and nutrient levels during the growth of the biomass.

C. Glucosamine Production Methods

The present invention is also directed to methods of forming glucosamine, including formation from acid hydrolysis of fermented microbial biomass, such as bacterial or fungal biomass. In the case of fungal biomass the acid hydrolysis breaks the ether linkages and deacetylates the chitin molecule to generate free glucosamine. Acid hydrolysis is strong enough to break the chitin into glucosamine, but leaves the glucosamine molecule substantially intact. The hydrolysis reaction conditions have the added advantage of breaking down some of the other components (such glucans, proteins, and lipids) that exist in both fungal and bacterial biomass. Typically, such acid hydrolysis is performed by treating the microbial biomass for between 1 and 10 hours. When working with bacterial biomass, or predominatly bacterial biomass, shorter treatment times may be used. For example, treatment from about 30 minutes to about 1.5 hours can be used when working with bacterially derived biomass. When working with fungal biomass, or predominantely fungal biomass, longer treatment times can be used. For example, incubation in acidic solutions for greater than 4 hours is not uncommon.

Glucosamine production usually includes the steps of providing chitin-containing biomass, reacting the chitin-containing biomass in an acidic solution to form glucosamine, and separating the glucosamine from the acidic solution. The reaction typically has a yield of glucosamine of greater than 50 percent of total chitin content of the fungal biomass starting material.

Strong acids can be used to hydrolyze the microbial biomass, including acids of concentrations less than 50 percent, and more commonly from 5 to 25 percent. Suitable strong acids include hydrochloric, sulfuric, phosphoric, and citric acid at appropriate levels.

The glucosamine forming reaction is normally conducted with 5 to 20 percent acid, 2 to 50 percent pretreated biomass (based upon dry weight, although the biomass is typically processed with water present), and 35 to 93 percent water. In certain implementations the reaction mixture comprises from 8 to 12 percent hydrochloric acid, from 4 to 8 percent biomass (based upon dry weight), and from 80 to 90 percent water.

The mixture containing the biomass, acid, and water is heated and maintained at an elevated temperature. The mixture is usually heated to a temperature at or near its boiling point and maintained under reflux conditions for greater than 5 hours, more typically greater than 8 hours, and usually less than 16 hours. It is desirable to have the reaction continue long enough to have a complete breakdown of the chitin, but not take so long as to be inefficient or to excessively decompose the glucosamine.

Reaction in the acid solution produces glucosamine, but subsequent purification steps are typically necessary to produce a satisfactory product. A first purification step normally includes filtration to remove particulate impurities, resulting in a substantially clear filtrate. This filtrate normally contains glucosamine, as well as small quantities of glucose and other sugars. An evaporative step can subsequently be performed to concentrate the glucosamine and possibly remove some of the acid, which can be recycled and reused. The mixture can be concentrated by evaporation, and the glucosamine can be precipitated out as purified solids by either adding ethanol to the concentrated mixture or continuing the evaporation to its solubility limits.

The glucosamine can be recovered by filtration or centrifugation, followed by drying. The dried glucosamine is optionally further purified to remove any residual sugar. One method of removing these excess sugars is by dissolving the glucosamine in water and adding ethanol, which precipitates the glucosamine at greater purity. Alternatively, the solution can be purified by electro dialysis, chromatography, membrane filtration, etc. The glucosamine is optionally decolorized with ethanol, carbon, or other suitable material and method.

In addition to the steps described above, the biomass can initially be treated to remove some impurities or to improve glucosamine production. These treatments can include heating the biomass, adding digestive enzymes, mixing with an acid or base, mechanical agitation, or dewatering by compression. One particularly suitable treatment is pretreating the biomass in the presence of sodium hydroxide. In certain implementations a concentration of less than 10 percent sodium hydroxide is added to the microbial biomass, which is heated to an elevated temperature for a period sufficient to remove a considerable portion of the non-chitin or non-murein containing material. This period is normally less than two hours. One specific example of this pretreatment method requires heating the microbial biomass to 100 to 125° C. in a 2 to 8 percent solution of sodium hydroxide for 20 to 60 minutes. This step hydrolyzes some protein and glucan in the biomass, the byproducts of which are optionally removed by filtration. The filtration step is followed to remove soluble proteins, amino acids, etc. In specific implementations of the invention, the washed and pretreated biomass contains greater than 50 percent water, and even greater than 70 or 80 percent water. Typically the water level is from about 80 to 95 percent for this prewashed microbial biomass.

D. Examples

The invention will be further explained by the following non-limiting illustrative examples. Unless otherwise indicated, all amounts are expressed in parts by weight.

Example 1

Citric biomass was pretreated with a 4 percent aqueous sodium hydroxide (NaOH) solution in an autoclave at 120° C. for 1 hour. This step removed excess proteins and other undesirable materials. The biomass was then thoroughly washed with de-ionized water until its pH was approximately 7.0. This washed material was mixed with concentrated hydrochloric acid (HCl) and water to form a mixture of 10 to 15 percent HCl and 5 to 6 percent biomass, based upon dry weight of the biomass. This mixture was heated at reflux. Samples were taken from time to time, and the reaction analyzed with a high-pressure liquid chromatograph available from Dionex HPLC under the trade designation "DX-500".

Figure 2:
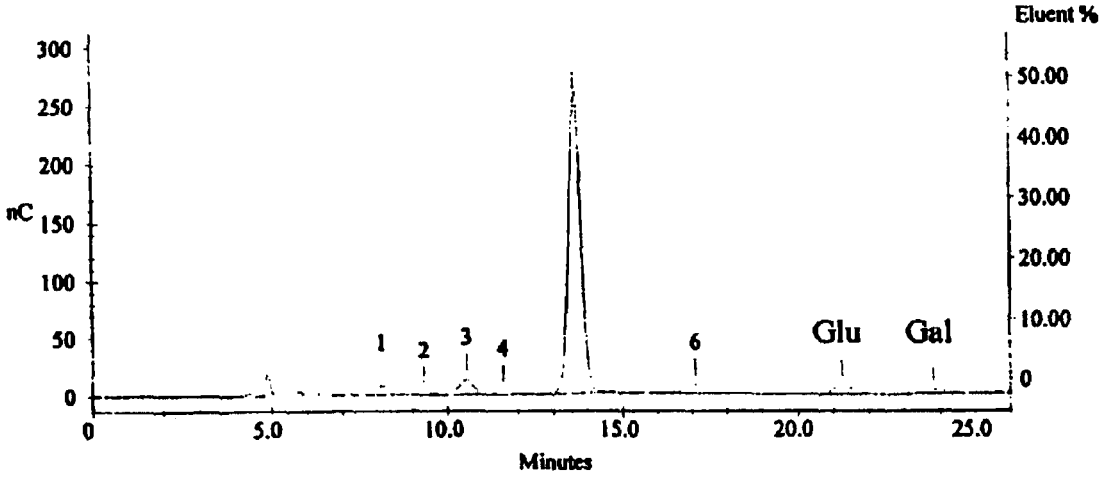
FIG. 2 is a chromatogram of glucosamine made in accordance with the invention.

The results are provided in FIG. 1, which shows a chart indicating glucosamine production, and shows that the glucosamine was increasingly produced as the reaction ran through 8 hours, but that the amount of glucose diminished after 4 hours. After 8 hours the glucosamine produced in the yield of 14 percent. A chromatogram of the product is shown in FIG. 2.

Figure 3:
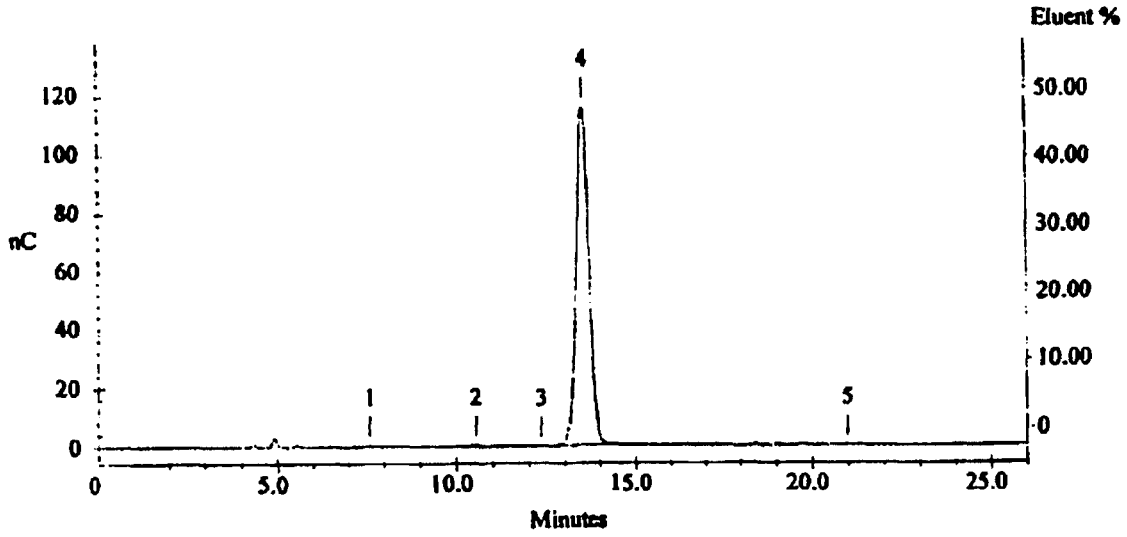
FIG. 3 is a chromatogram of glucosamine made in accordance with the invention.

Following reaction, the mixture was filtered, and the filtrate evaporated using a rotating evaporator manufactured by RotaVap to increase the glucosamine concentration of the solution. The final volume was reduced to about 10 to 20 ml. To this solution was added 20 ml of ethanol and the solution swirled to promote precipitation of glucosamine and enhance yield. These glucosamine precipitates were obtained by filtration and were further washed with alcohol until the color became white. FIG. 3 shows a chromatogram of the product, indicating greater than 97 percent glucosamine.

Example 2

Example 1 was repeated, but the pretreated biomass was maintained under reflux conditions for 13 hours. The resulting glucosamine was greater than 98 percent pure.

The foregoing detailed description and examples have been given for clarity of understanding only. No unnecessary limitations are to be understood from this description or examples. The invention is not limited to the exact details shown and described, for variations will be included within the invention defined by the claims.

Example 3

The Gram-positive bacteria *Streptomyces griseus* and *Bacillus subtilis* were isolated as individual colonies on trypticase-soya agar for growth in pure culture. Each was separately inoculated into 1 L of sterile trypticase-soya broth and grown for 48 hours at 32° C. and 170 rpm. The mature cultures were harvested by centrifugation for 10 minutes at 7,500 g and 4° C. Each pellet was washed in 50 mL of phosphate buffer and centrifuged as above. The pellets of bacterial biomass were stored at −20° C. until processing.

Additionally, three cultures of unknown gram positive bacteria were isolated as single colonies on Tripticase Soy Agar (TSA) from corn gluten meal. Each culture was further isolated as a pure culture by streaking on TSA, and subsequently characterized by Gram staining. The unknown cultures were classified as unique from one another based on the differences between the types of colonies they formed and their cellular morphologies. These cultures were grown and frozen down using the same process described above.

Figure 4:
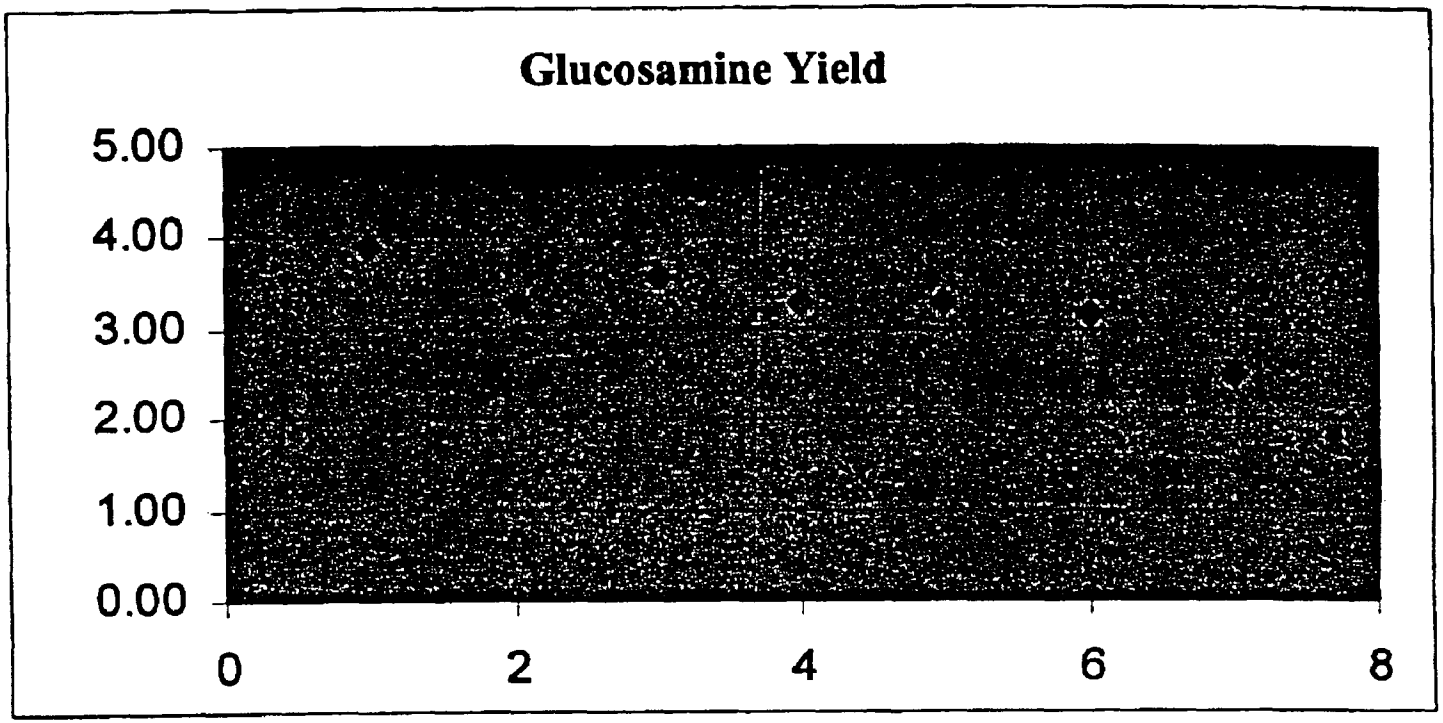
FIG. 4 is a chart showing the percent yield of glucosamine over time. The biomass used as a starting material is derived from a culture of *Bacillus subtilis.*
Figure 5:
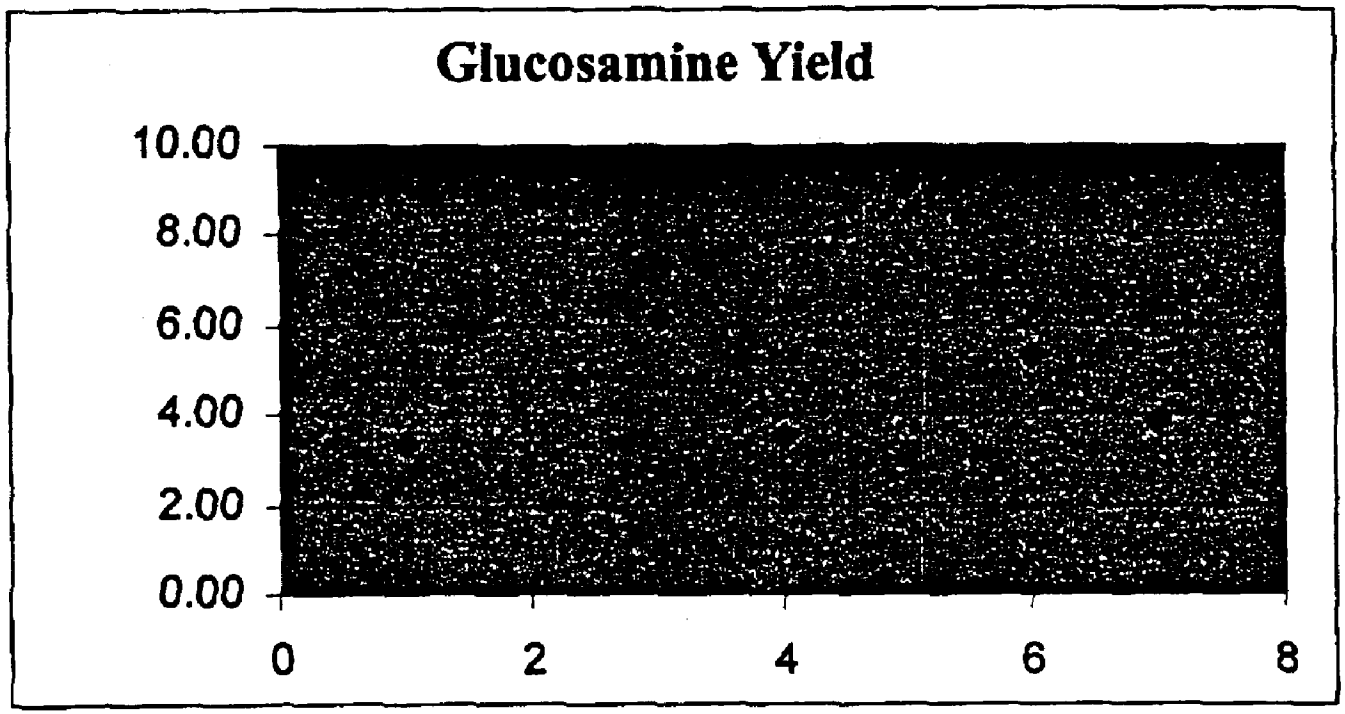
FIG. 5 is a chart showing the percent yield of glucosamine over time. The biomass used as a starting material is derived from a culture of *Streptomyces griseus.*
Figure 6:
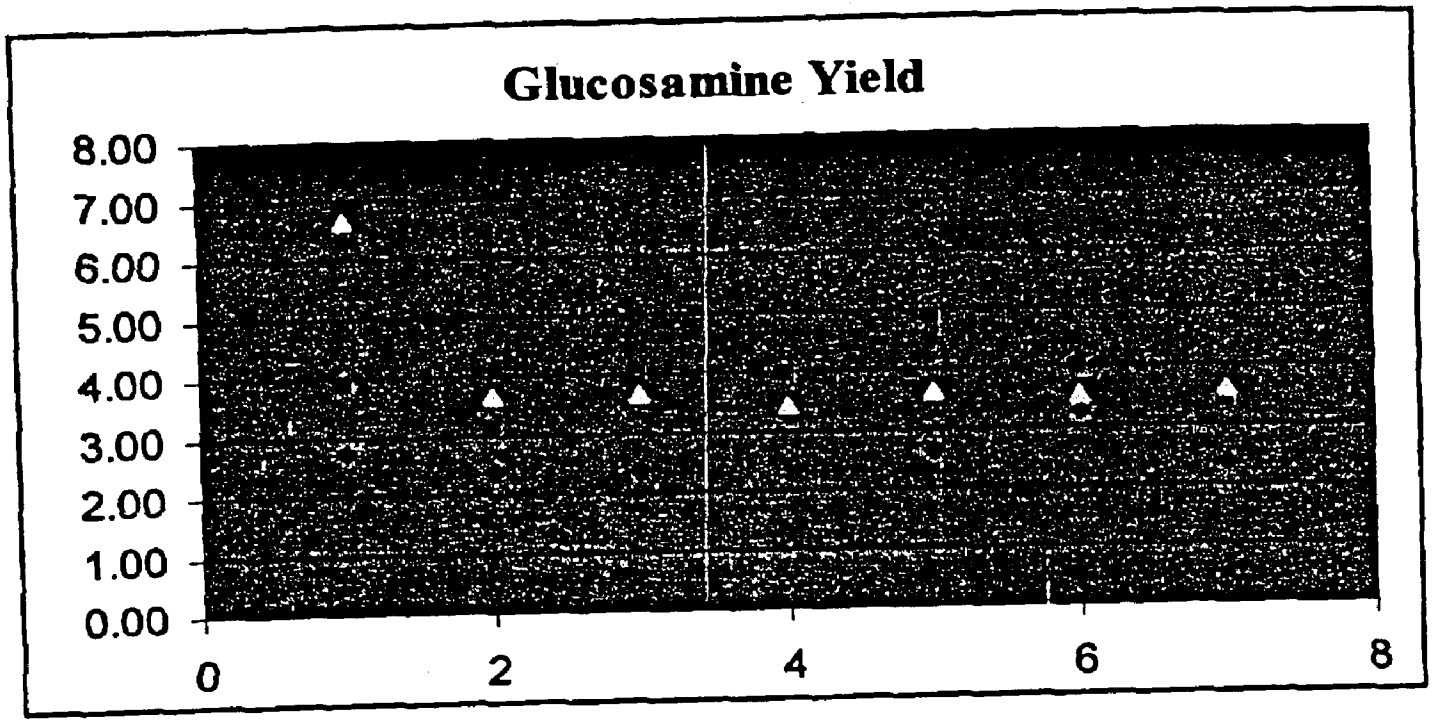
FIG. 6 is a chart showing the percent yield of glucosamine over time for three Gram-positive bacterial cultures. The cultures were isollated from corn meal.

Glucosamine was isolated from the samples using the methodology described in Example 1, above. Results are shown graphically in FIGS. 4–6, for *Bacillus subtillis, Streptomyces griseus,* and the unknown cultures (A, B, and C), respectively.

We claim:

1. A glucosamine containing material suitable for human or animal consumption, the glucosamine derived from fermented microbial biomass.

2. The glucosamine containing material of claim 1, wherein the glucosamine has an ash content below 2 percent.

3. The glucosanine containing material of claim 1, wherein the glucosamine has a heavy metal content below 20 parts per million.

4. The glucosamine containing material of claim 1, wherein the glucosamine is formed by acid hydrolysis of the fermented microbial biomass.

5. The glucosamine containing material of claim 4, wherein the glucosamine is formed by acid hydrolysis of microbial biomass by treating the microbial biomass with acid for greater than 4 hours.

6. The glucosamine containing material of claim 4, wherein the glucosamine is formed by acid hydrolysis of microbial biomass by treating the biomass with acid for greater than 8 hours.

7. The glucosamine containing material of claim 4, wherein the glucosamine is formed by acid hydrolysis of microbial biomass by treating the biomass with a 5 to 25 percent strong acid solution.

8. The glucosamine containing material of claim 4, wherein the glucosamine is formed by acid hydrolysis of microbial biomass by treating the biomass with a 5 to 25 percent strong acid solution for greater than 4 hours.

9. The glucosamine containing material of claim 1, wherein the glucosamine has a positive 69 to 74 degree specific rotation when the glucosamine is in the form of a hydrochloride salt.

10. The glucosamine containing material of claim 1, wherein the microbial biomass has a yield of greater than 50 percent of total chitin content of the biomass starting material.

11. The glucosamine containing material of claim 1, wherein the glucosamine containing material contains less than 5 percent glucose.

12. The glucosamine containing material of claim 1, wherein the glucosamine containing material is greater than 98 percent pure based upon dry weight.

13. The glucosamine containing material of claim 12, wherein the glucosamine containing material comprises glucosamine alone, or glucosamine mixed with additional ingredients.

14. The glucosamine containing material of claim 1, wherein a 20 percent by weight aqueous solution of the glucosamine has an American Public Health Association color of less than 50.

15. The glucosamine containing material of claim 1, wherein the glucosamine is derived from substantially uniform microbial fungal sources.

16. The glucosamine containing material of claim 15, wherein the glucosamine is derived from *Aspergillus* sp., *Penicillium* sp., *Mucor* sp. and combinations thereof.

17. The glucosamine containing material of claim 15, wherein the glucosamine is derived from species of filamentous fungi having greater than 10 chitin percent by total cell weight.

18. A method of obtaining glucosamine from microbial biomass, the method comprising the steps of:

(a) providing chitin-containing biomass;

(b) reacting the chitin-containing biomass in an acidic solution with an acid concentration of greater than 5 percent at a reaction temperature greater than 80° C. for a reaction period of at least 4 hours to convert chitin in the biomass to glucosamine; and (c) separating the glucosamine from the acidic solution.

19. The method of claim 18, wherein the step of separating the glucosamine comprises crystallization of the glucosamine from the acidic solution.

20. The method of claim 18, wherein the acid solution has an acid concentration of 5 to 25 percent.

21. The method of claim 18, wherein the acid solution has an acid concentration of 5 to 50 percent.

22. The method of claim 18, wherein the reaction temperature is above 80° C.

23. The method of claim 18, wherein the reaction period is from 4 to 25 hours.

24. The method of claim 18, wherein the glucosamine containing material has a yield of greater than 50 percent of total chitin content of the chitin-containing biomass and contains less than 5 percent glucose.

25. The method of claim 18, wherein the glucosamine containing material contains less than 5 percent soluble sugars.

26. The method of claim 18, wherein the glucosamine containing material is greater than 98 percent glucosamine based upon dry weight.

27. The method of claim 18, wherein the glucosamine is derived from *Aspergillus* sp., *Penicillium* sp., *Mucor* sp. and combinations thereof.

* * * * *